(12) United States Patent
Gryska et al.

(10) Patent No.: US 9,599,583 B2
(45) Date of Patent: *Mar. 21, 2017

(54) HUMIDITY SENSOR AND SENSOR ELEMENT THEREFOR

(75) Inventors: Stefan H. Gryska, Woodbury, MN (US); Michael C. Palazzotto, Woodbury, MN (US); Krzysztof A. Lewinski, Mahtomedi, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 522 days.

This patent is subject to a terminal disclaimer.

(21) Appl. No.: 14/115,514

(22) PCT Filed: May 30, 2012

(86) PCT No.: PCT/US2012/039996
§ 371 (c)(1),
(2), (4) Date: Nov. 4, 2013

(87) PCT Pub. No.: WO2012/170248
PCT Pub. Date: Dec. 13, 2012

(65) Prior Publication Data
US 2014/0076048 A1    Mar. 20, 2014

Related U.S. Application Data

(60) Provisional application No. 61/494,578, filed on Jun. 8, 2011.

(51) Int. Cl.
*G01N 27/22* (2006.01)
*G01N 27/04* (2006.01)
*G01N 27/12* (2006.01)

(52) U.S. Cl.
CPC ......... *G01N 27/223* (2013.01); *G01N 27/048* (2013.01); *G01N 27/121* (2013.01)

(58) Field of Classification Search
CPC ... G01N 27/223; G01N 27/048; G01N 27/121
(Continued)

(56) References Cited

U.S. PATENT DOCUMENTS 4,305,112 A * 12/1981 Heywang ............ G01N 27/225
361/286
4,549,134 A    10/1985 Weiss
(Continued)

FOREIGN PATENT DOCUMENTS

CN    1043987 A    7/1990
CN    2080670 U    7/1991
(Continued)

OTHER PUBLICATIONS

International Search Report for PCT International Application No. PCT/US2012/039996, mailed on Sep. 5, 2012, 3 pages.
(Continued)

*Primary Examiner* — Hezron E Williams
*Assistant Examiner* — Marrit Eyassu
(74) *Attorney, Agent, or Firm* — Yufeng Dong; Bradford B. Wright

(57) ABSTRACT

A humidity sensor element includes a dielectric substrate, a nonporous conductive electrode disposed on the dielectric substrate, a permeable conductive electrode having a thickness in a range of from 4 to 10 nanometers and permeable by water vapor, and a detection layer sandwiched between the nonporous conductive electrode and the permeable conductive electrode. The permeable conductive electrode is parallel to the nonporous electrode. Both conductive electrodes have respective conductive leads attached thereto. The detection layer includes a copolymer having monomeric units comprising wherein M represents H, or an alkali metal. A humidity sensor including the humidity sensor element is also disclosed.

(Continued)

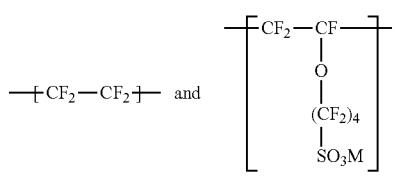

13 Claims, 1 Drawing Sheet

(58) Field of Classification Search
USPC .................................................... 63/335.04
See application file for complete search history.

(56) References Cited

U.S. PATENT DOCUMENTS

| | | | |
|---|---|---|---|
| 4,662,220 A | 5/1987 | Laue | |
| 4,681,855 A * | 7/1987 | Huang | G01N 21/81 |
| | | | 338/35 |
| 4,693,953 A | 9/1987 | Torikai | |
| 4,858,063 A | 8/1989 | Laue | |
| 4,920,451 A * | 4/1990 | Sakai | G01N 27/225 |
| | | | 361/286 |
| 5,014,908 A | 5/1991 | Cox | |
| 5,036,704 A | 8/1991 | Pusatcioglu | |
| 5,050,434 A * | 9/1991 | Demisch | G01N 27/225 |
| | | | 361/286 |
| 5,296,819 A * | 3/1994 | Kuroiwa | G01N 27/225 |
| | | | 324/664 |
| 5,408,381 A * | 4/1995 | Thoma | G01N 27/225 |
| | | | 29/25.42 |
| 6,724,612 B2 * | 4/2004 | Davis | G01N 27/225 |
| | | | 361/280 |
| 7,270,002 B2 * | 9/2007 | Chen | B82Y 30/00 |
| | | | 29/25.35 |
| 7,348,088 B2 | 3/2008 | Hamrock | |
| 7,449,146 B2 | 11/2008 | Rakow | |
| 8,378,694 B2 | 2/2013 | David | |
| 8,409,511 B2 | 4/2013 | Thomas | |
| 8,537,358 B2 | 9/2013 | Rakow | |
| 8,564,740 B2 | 10/2013 | Schultz | |
| 2001/0015089 A1 | 8/2001 | Kleinhans | |
| 2003/0056571 A1 * | 3/2003 | Shibue | G01N 27/121 |
| | | | 73/29.01 |
| 2004/0036394 A1 | 2/2004 | Hamrock | |
| 2005/0095487 A1 * | 5/2005 | Hamrock | C08F 14/18 |
| | | | 429/428 |
| 2008/0063575 A1 | 3/2008 | Rakow | |
| 2008/0063874 A1 | 3/2008 | Rakow | |
| 2010/0005881 A1 * | 1/2010 | Broedel | G01N 33/0059 |
| | | | 73/335.02 |
| 2010/0189600 A1 | 7/2010 | Hulteen | |
| 2011/0031983 A1 | 2/2011 | David | |
| 2011/0045601 A1 | 2/2011 | Gryska | |
| 2012/0062892 A1 | 3/2012 | Wendland | |
| 2013/0088244 A1 | 4/2013 | Gryska | |
| 2013/0186177 A1 | 7/2013 | Palazzotto | |

FOREIGN PATENT DOCUMENTS

| | | | | |
|---|---|---|---|---|
| CN | 1657927 A | 8/2005 | | |
| CN | 101447576 A | 6/2009 | | |
| CN | 101949878 A | 1/2011 | | |
| JP | H6-281610 | 10/1994 | | |
| JP | 2006-071647 | 3/2006 | | |
| JP | 2006071647 A * | 3/2006 | | G01N 27/22 |
| JP | 2007-517088 | 6/2007 | | |
| WO | WO 2009-045733 | 4/2009 | | |
| WO | WO 2010-075333 | 7/2010 | | |
| WO | WO 2010-135413 | 11/2010 | | |
| WO | WO 2010-135417 | 11/2010 | | |
| WO | WO 2012-044419 | 4/2012 | | |
| WO | WO 2012-050686 | 4/2012 | | |
| WO | WO 2012-141894 | 10/2012 | | |
| WO | WO 2012-141958 | 10/2012 | | |

OTHER PUBLICATIONS

Hamrock "Membranes for PEM Fuel Cells", GRC Membranes: Materials and Process, Aug. 2008, 73 pages.

Su, "A microfabricated amperometric moisture sensor," Talanta, Feb. 2002, vol. 56, No. 2, pp. 309-321.

Tailoka, "Application of Nafion electrolytes for the detection of humidity in a corrosive atmosphere" Solid State Ionics, Aug. 2003, vol. 161, No. 3-4, pp. 267-277.

Wu, "Composite of $TiO_2$ nanowires and Nafion as humidity sensor material", Sensors and Actuators B: Chemical, May 2006, vol. 115, No. 1, pp. 198-204.

Wendland, U.S. Appl. No. 61/415,195, entitled "Humidity Sensor and Humidity Indicator System," and filed Feb. Nov. 18, 200.

* cited by examiner

HUMIDITY SENSOR AND SENSOR ELEMENT THEREFOR

FIELD

The present disclosure broadly relates to capacitance-type sensor elements and humidity sensors.

BACKGROUND

Humidity sensors are widely used in the monitoring and control of industrial processes, environmental applications, electronic and biotechnology sectors, agriculture, libraries and household applications. In the last few years an increasing demand has developed for low cost humidity sensors with high accuracy, good reproducibility and long-term stability. Unfortunately good humidity sensors are very expensive and most of the inexpensive ones do not perform well at above 70 percent or below 20 percent relative humidity.

Capacitive humidity sensors have been constructed by sandwiching a humidity-sensitive material between two parallel electrodes. Sulfonated fluoropolymers have been used as the humidity-sensitive material because of their excellent thermal and mechanical stability, and the capability of extremely fast and accurate response to change in humidity.

One of the most widely used sulfonated fluoropolymers in construction of humidity sensors include copolymers of $CF_2=CFOCF_2CF(CF_3)OCF_2CF_2SO_3H$ and tetrafluoroethylene. Polymers of this type are available under the trade designation NAFION from E. I. du Pont de Nemours and Company of Wilmington, Del. For example, U.S. Pat. No. 4,662,220 (Laue) reports a method and apparatus using a known water-absorbent polymer as a capacitor which is operated at a DC voltage for measuring relative humidity. When formed as a layer between porous electrically-conductive electrodes and operated in an RC oscillator circuit, the oscillator frequency varies inversely with the partial pressure of the moisture to be measured. In a preferred embodiment, the capacitor is formed from a NAFION polymer.

U.S. Pat. No. 5,036,704 (Pusatcioglu et al.) reports a moisture sensor that utilizes a sulfonated fluorocarbon film having a thickness of less than about one micron and capable of providing accurate measurements of humidity and extremely fast response to change in humidity. A preferred embodiment of an electrical system is disclosed for use with sensor, and a sulfonated tetrafluoroethylene perfluoroether copolymer form of the film is especially preferred.

SUMMARY

In one aspect, the present disclosure provides a humidity sensor element comprising:
 a dielectric substrate;
 a nonporous conductive electrode having a first conductive member electrically coupled thereto, wherein the nonporous conductive electrode is disposed on the dielectric substrate;
 a permeable conductive electrode having a second conductive member electrically coupled thereto, wherein the permeable conductive electrode has a thickness in a range of from 4 to 10 nanometers, and wherein the permeable conductive electrode is permeable by water vapor;
 a detection layer sandwiched between the nonporous conductive electrode and the permeable conductive electrode, wherein the detection layer comprises a copolymer having monomeric units comprising

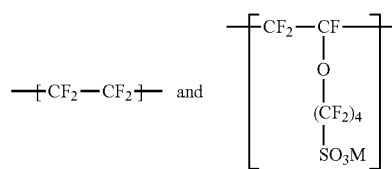

wherein M represents H, or an alkali metal (e.g., Li, Na, or K).

Humidity sensor elements according to the present disclosure are useful, for example, for incorporation into humidity sensors. Accordingly, in another aspect, the present disclosure provides a humidity sensor comprising:
 a sensor chamber having an inlet opening;
 a humidity sensor element according to the present disclosure and having a capacitance, wherein the humidity sensor element is disposed within the sensor chamber in fluid communication with the inlet opening; and
 an operating circuit in electrical communication with the first and second conductive leads of the humidity sensor element, whereby if the humidity sensor element is connected to a source of electrical power, the operating circuit measures the capacitance of the sensor element.

Humidity sensor elements used in the present disclosure may have better reliability and/or durability, especially at elevated temperatures.

As used, herein the term "wherein the permeable conductive electrode is permeable by water vapor" means that water vapor is capable of passing through the bulk material comprising the conductive electrode for a distance of at least its full thickness, and does not refer to passage through perforations or other such intentionally provided openings in the conductive electrode.

As used herein, "sulfonate equivalent weight" refers to as the weight of the polymer (in grams) per mole of sulfonic acid and sulfonate groups combined.

Sulfonated fluoropolymer-based capacitive sensors may be very sensitive to change in humidity over the entire range of percent. They can be used, for example, in household applications to automatically turn on/off bathroom fan based on the relative humidity or in challenging industrial applications to monitor corrosive gases for their moisture level. These sensors offer good selectivity and permeability to water vapors and their response time is comparable to commercial units.

The features and advantages of the present disclosure will be further understood upon consideration of the detailed description as well as the appended claims.

In all cases, the disclosure is presented by way of representation and not limitation. It should be understood that numerous other modifications and embodiments can be devised by those skilled in the art, which fall within the scope and spirit of the principles of the disclosure. The figure may not be drawn to scale.

DETAILED DESCRIPTION

Figure 1:
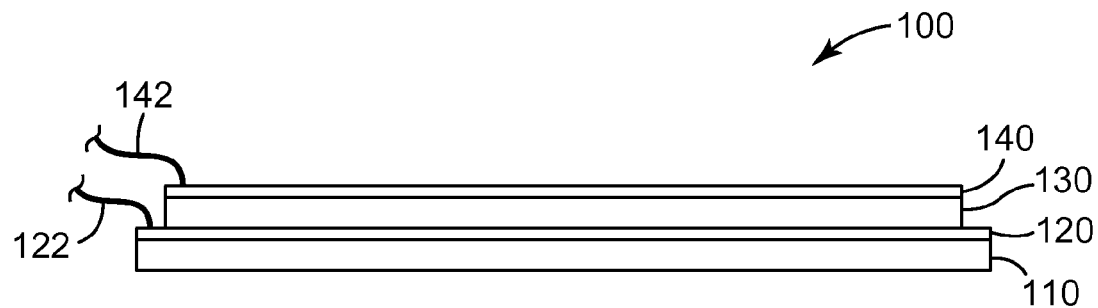
FIG. 1 is a schematic side view of an exemplary sensor element 100 according to the present disclosure.

Referring now to FIG. 1, exemplary humidity sensor element 100 comprises dielectric substrate 110, nonporous conductive electrode 120 disposed on substrate 110, permeable conductive electrode 140, and detection layer 130, sandwiched between nonporous conductive electrode 120 and permeable conductive electrode 140. First and second conductive members (122, 142) are electrically coupled to nonporous conductive electrode 120 and permeable conductive electrode 140, respectively. Permeable conductive electrode 140 has a thickness in a range of from 4 to 10 nanometers, and is permeable by water vapor. Detection layer 130 comprises a copolymer having monomeric units comprising

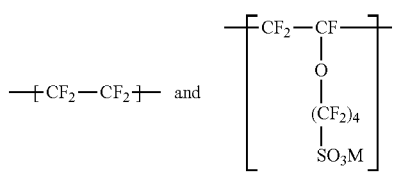

wherein M represents H, or an alkali metal.

Dielectric substrate 110 may comprise any dielectric material that may serve to provide physical strength and integrity to the sensor element. Suitable materials include glasses, ceramics, stone, minerals (e.g., alpha alumina or sapphire), thermoplastics (e.g., polyesters, polycarbonates, polyamides, polyimides, and polyether ether ketones) and thermosets (e.g., Bakelite and cured epoxy resins). In large scale production, a polymeric film (such as polyester) may be used. In some embodiments, the dielectric substrate is nonporous, although this is not a requirement as long as it can support the nonporous conductive electrode. Similarly, it is typically at least coextensive with the nonporous conductive electrode, although this is not a requirement as long as it can support the nonporous conductive electrode. In some embodiments, the dielectric substrate comprises a glass plate.

Nonporous conductive electrode 120 may comprise any conductive material, desirably a corrosion-resistant conductive material. Combinations of different materials (conductive and/or nonconductive) can be used, as different layers or as a mixture, as long as sufficient overall conductivity is provided, Typically, the nonporous conductive electrode has a sheet resistance of less than about $10^7$ ohms/square, although higher sheet resistances may also be used. Examples of materials that can be used to make the nonporous conductive electrode include: organic materials, inorganic materials, metals and their alloys, and combinations thereof. In certain embodiments, coated (e.g., thermal-vapor-coated, sputter-coated) metals or metal oxides, or combinations thereof, may be used. Suitable conductive materials include for example aluminum, nickel, titanium, tin, indium-tin oxide, gold, silver, platinum, palladium, copper, chromium, carbon (e.g., including carbon nanotubes), and combinations thereof. In some embodiments, the conductive material is selected from titanium, gold, platinum, and combinations thereof. Desirably, to avoid corrosion, a noble metal component of the nonporous electrode is in contact with the detection layer.

The nonporous conductive electrode has a thickness in a range of from at least 4 nm to 400 nm, or from 10 nm to 200 nm.

Detection layer 120 comprises a copolymer having monomeric units comprising

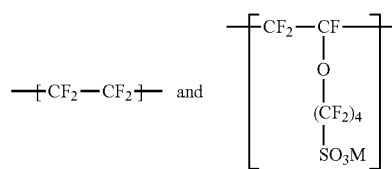

wherein M represents H (i.e., hydrogen), or an alkali metal (e.g., lithium, sodium, or potassium).

Such copolymers are described, for example, in U.S. Pat. No. 7,348,088 (Hamrock et al.), the disclosure of which is incorporated herein by reference. In one embodiment, the copolymer may be a random copolymer having a segment represented by the stoichiometric formula

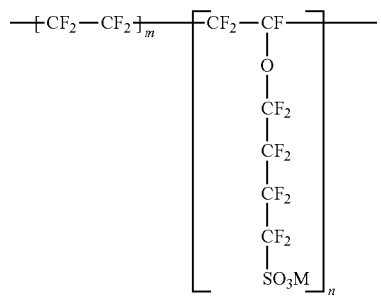

wherein m and n are positive integers (i.e., 1, 2, 3, etc.), and M is as previously defined. Other pendant groups such as, for example, perfluoroalkyl groups or perfluoroalkoxyl groups may also be present. Typically, substantially no (e.g., less than 5 mole percent of) other pendant groups are present in the copolymer; and more typically, no other pendant groups are present.

The copolymer may be made by the copolymerization of tetrafluoroethylene with 4'-fluorosulfonyl-1',1',2',2',3',3',4',4'-octafluorobutyloxy-1,2,2- trifluoroethylene (i.e., $CF_2$=$CFO(CF_2)_4SO_2F$) followed by basic hydrolysis of the sulfonyl fluoride to the alkali metal sulfonate form or the sulfonic acid form. Additional co-monomers may be included to provide perfluoroalkyl or perfluoroalkyl ether pendant groups in the copolymer. Vinylidene fluoride may also be used as a monomer. Polymerization can be accomplished by any suitable method, including aqueous emulsion polymerization. The copolymer typically may have a sulfonate equivalent weight (i.e., the weight of the copolymer having one —$SO_3M$ group) of at least 500 grams per sulfonate equivalent, more typically at least 650 grams per sulfonate equivalent, and more typically at least 750 grams per sulfonate equivalent. The copolymer typically has a sulfonate equivalent weight of less than 1200 grams per sulfonate equivalent, more typically less than 1100 grams per sulfonate equivalent, or even less than or equal to 1000 grams per sulfonate equivalent. In some embodiments, the copolymer has a sulfonate equivalent weight in a range of from 500 to 1000 grams per sulfonate equivalent.

Examples of commercially available copolymers include those available under the trade designation 3M PERFLUOROSULFONIC ACID IONOMER from 3M Company, Saint Paul, Minn.

The detection layer may be deposited (for example, on the nonporous conductive layer) by any suitable technique. Casting out of solvent or water, followed by heating to dry and optionally anneal the detection layer is typically an effective method. If desired, a fluorosulfonylated precursor copolymer may be cast out of solvent followed by hydrolysis, as discussed above.

The detection layer may have any thickness, but typically is in a range of from about 100 nanometers (nm) to 1 millimeter. More typically, the detection layer has a thickness in a range of from 500 nm to 10 microns, or even from 700 to 3500 nm.

The detection layer may contain additional additions such as, for example, colorants, residual organic solvent, fillers, or plasticizers; however, as such additives may be detrimental, the detection layer typically consists essentially (or consists) of the above-described copolymer.

Permeable conductive electrode 140 is permeable to water vapor and conductive. Typically, permeable conductive electrode has a sheet resistance of less than about $10^7$ ohms/square, although higher sheet resistances may also be used.

In some embodiments, the permeable conductive electrode comprises at least one noble metal (e.g., gold, platinum, palladium, or a combination thereof). In some embodiments, the permeable conductive electrode may have a noble metal content of at least 50, 60, 70, 80, 90, 95, 99, or even at least 99.9 percent by weight. In some embodiments, the permeable conductive electrode consists of, or consists essentially of gold, palladium, platinum, or a combination thereof. The second layer may include additional components as long as it remains permeable to water vapor. Combinations of different materials (conductive and/or nonconductive) can be used, as different layers or as a mixture, as long as sufficient overall conductivity and permeability is provided. Typically, the permeable conductive electrode has a sheet resistance of less than about $10^7$ ohms/square.

The permeable conductive electrode has a thickness in a range of from 4 to 10 nanometers (nm). In some embodiments, the permeable conductive electrode has a thickness in a range of from 5, 6, or 7 nm up to 8, 9, or 10 nm. For example, the permeable conductive electrode may have a thickness in a range of from 5 nm to 8 nm, or from 6 nm to 7 nm. Greater thicknesses generally have undesirably low levels of permeability, while lesser thicknesses may become insufficiently conductive and/or difficult to electrically connect to the second conductive member. Since the permeable conductive electrode is permeable, the first electrode typically comprises a continuous, uninterrupted layer, but it may contain openings or other interruptions if desired.

The permeable conductive electrode can be prepared by a thermal vapor deposition process. In thermal vapor deposition, the material used to make the permeable conductive electrode is heated under vacuum until it vaporizes and deposits on an appropriate component of the humidity sensor element (e.g., detection layer 120). Any suitable source of heating may be used; examples include resistive heating, laser heating, and e-beam heating (also termed e-beam evaporation). Thermal vapor deposition is generally carried out at pressures of about $10^{-5}$ or $10^{-6}$ torr (1 mPa-0.1 mPa) or less.

Thermal vapor deposition differs from sputter deposition. In sputter deposition, high energy atoms are bombarded into a target or source which then ejects material that deposits on a substrate. Typical pressures involved in sputter deposition are in the range of $10^{-2}$–$10^{-4}$ torr (1 Pa-0.1 Pa) or higher.

First and second conductive members (122, 142) may be formed of any conductive material such as, for example, metal (e.g., gold or copper), carbon, and/or conductive oxide. First and second conductive members (122, 142) may comprise, for example, wires, traces, or a combination thereof. They may be electrically coupled to the permeable and nonporous conductive electrodes at any appropriate point during assembly of the sensor element. For example, the first conductive member 122 may be attached to the nonporous conductive electrode 120 immediately after deposition of the nonporous conductive electrode and before deposition of the detection layer.

Figure 2:
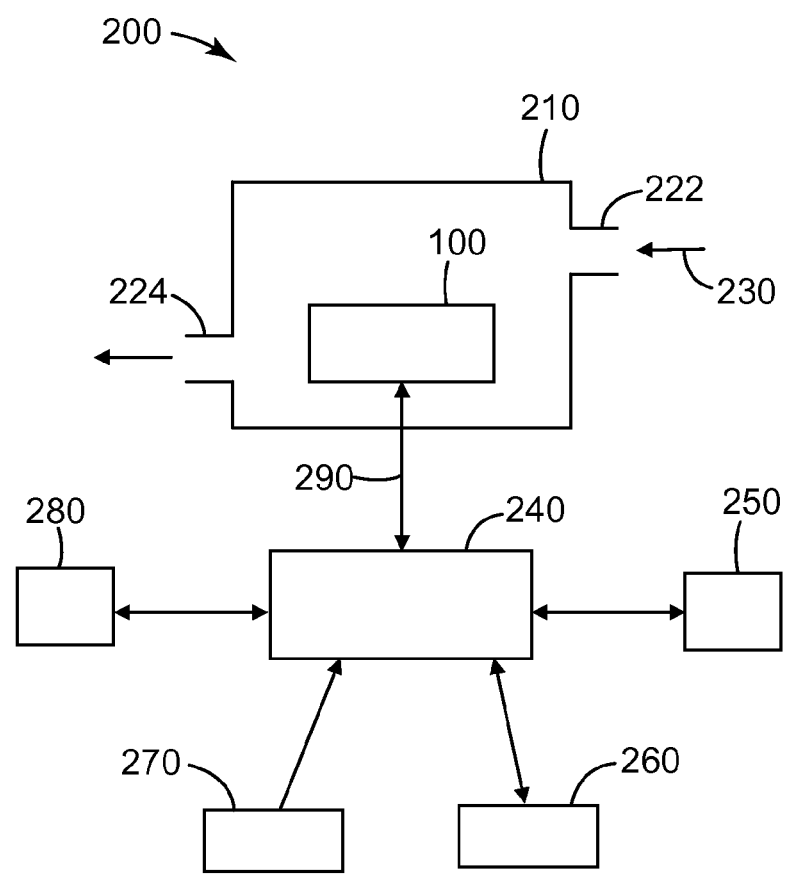
FIG. 2 is a schematic plan view of an exemplary humidity sensor 200 according to the present disclosure.

Referring now to FIG. 2, exemplary humidity sensor 200 includes a sensor chamber 210 having an inlet opening 222 and optional outlet opening 224. Humidity sensor element 100 (as described hereinabove) is disposed within the sensor chamber 210, and is in fluid communication with the inlet opening 222 and optional outlet opening 224, if present. In typical operation, a sample containing water vapor 230 enters sensing chamber 210 where it contacts humidity sensor element 100. Operating circuit 240 is in electrical communication via conductive pathways 290 with humidity sensor element 100. When connected to a source of electrical power 270, operating circuit 240 measures the capacitance of humidity sensor element 100. In some embodiments, operating circuit 240 is communicatively coupled to data storage device 250, controller device 280, and/or display device 260.

Operating circuit 240 can have any suitable design, for example, as will be known to those of skill in the art. For example, the operating circuit may comprise an LCR meter, a multimeter, or other electronic measurement device.

In operation, the operating circuit 240 is in electrical communication with a source of electrical power 270.

Exemplary sources of electrical power include batteries, plug in power supplies, generators, hardwired power supplies, and RF generators (e.g., if the operating circuit includes an RF receiver).

The sensor chamber can be constructed of any solid material that is impermeable to the water vapor. Examples include metal and/or plastic. Exemplary display devices 260 include LED displays, LCD displays, CRT displays, galvanic meters, and printers. Controller device 280, if present, includes hardware and/or software that directs operation of the operating circuit. Exemplary data storage devices 250 include flash memory cards, hard disks, digital tape, and CD-R media.

Humidity sensor elements and sensor devices according to the present disclosure can be used to detect and/or monitor (e.g., qualitatively or quantitatively) humidity levels of air, and may also be used to detect other analytes that are adsorbed/absorbed by the detection layer.

Upon absorption of sufficient water vapor by the detection layer, a detectable change in an electrical property associated with the humidity sensor element (e.g., capacitance, impedance, inductance, admittance, current, or resistance) may occur. Such a detectable change may be detected by an operating circuit that is in electrical communication with the nonporous conductive electrode and the permeable conductive electrode. In this context, "operating circuit" refers generally to an electrical apparatus that can be used to apply a voltage to the nonporous conductive electrode and the permeable conductive electrode (thus imparting a charge differential to the electrodes), and/or to monitor an electrical property of the sensor element, wherein the electrical property may change in response to the presence of water vapor. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. The operating circuit is typically electrically coupled to nonporous conductive electrode and the permeable conductive electrode by the first and second conductive members.

Humidity sensor elements according to the present disclosure are useful, for example, as sensor elements in humidity sensors, for example, as discussed above.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Preparation of Specimens

Glass slides (glass number 0050-0050-0010-GF-CA, 50 mm×50 mm, 1.1 mm thick, material C-263, surface 80/50, from Precision Glass & Optics, Santa Ana, Calif.) were cleaned by soaking for 30-60 minutes in ALCONOX LIQUI-NOX detergent solution from Alconox, Inc., White Plains, N.Y., then scrubbing each side of the slides with a bristle brush, rinsing under warm tap water followed by a final rinse with deionized water. The slides were allowed to air dry covered to prevent dust accumulation on the surface. The dry, clean slides were stored in 3-inch (7.6-cm) wafer carriers from Entegris, Chaska, Minn.

Nonporous conductive electrodes were deposited onto the clean glass slides by thermal vapor coating 5.0 nanometers (nm) of titanium followed by 20.0 nm of gold using a square mask (MASK A) having a single rectangular opening with a top border of 0.46 inch (1.2 cm), a bottom border of 0.59 inch (1.5 cm), and left and right borders of 0.14 inch (0.35 cm) prepared from laser-cut 1.16 mm thick stainless steel. The deposition process was controlled using an INFICON XTC/2 THIN FILM DEPOSITION CONTROLLER from INFICON, East Syracuse, N.Y.

Next, the nonporous conductive electrodes were spin coated with a solution/dispersion of sulfonated fluoropolymer (3M PERFLUOROSULFONIC ACID IONOMER (825 grams per sulfonate equivalent, 3M Company, St. Paul, Minn., or NAFION DE2820 copolymer, E.I. du Pont de Nemours & Co., Wilmington, Del.) using a Model WS 400B-8NPP/LITE spin coater from Laurell Technologies Corporation, North Wales, Pa. Each specimen to be coated was placed in the spin coater and about 0.5 ml of methanol was placed on the sample. Each sample was spun for 60 seconds at a specific rotational speed (rpm) as indicated. Then, for all specimens, about one mL of sulfonated fluoropolymer solution/dispersion was dispensed on the sample and spun for 60 seconds at specific rpm (see examples). After spin coating, thickness measurements of the sulfonated fluoropolymer (i.e., detection layer) were made using a Model XP-1 Profilometer from AMBiOS Technology of Santa Cruz, Calif. All samples were baked for one hour at 150° C. after coating.

The permeable conductive electrode was vapor deposited through a 2 inches (5 cm)×2 inches (5 cm) mask (MASK B) having a 2×2 regular array of four 0.60 inch (1.5 cm) height×0.33 inch (0.84 cm) width rectangular openings vertically separated by 0.22 inch (0.56 cm) and horizontally separated by 0.48 inch (1.2 cm) was made from 24 gauge stainless steel by laser milling using thermal deposition of gold at 6 nm thickness. After depositing the permeable conductive electrode, connecting electrodes were deposited by thermal vapor coating 5.0 nm of titanium followed by 20.0 nm of gold through a 2 inches (5 cm)×2 inches (5 cm) mask (MASK C) having two horizontal rectangular openings with a height of 0.4 inch (1 cm), left and right borders of 0.14 inch (0.36 cm), and a separation of 0.92 inch (2.4 cm), prepared by laser milling from 50 gauge stainless. The deposition process was controlled using an INFICON XTC/2 THIN FILM DEPOSITION CONTROLLER.

This specimen preparation process produced a set of 4 specimens of approximately 5 mm×6 mm active area (area sandwiched between the permeable conductive electrode and the nonporous conductive electrode) disposed on an approximately 50 mm×50 mm glass substrate. Individual specimens were produced by dicing the specimen using a standard glass scoring cutter on the back (inactive side) while supporting the specimens so that their front (active) surfaces would not be damaged. After dicing, individual specimens were tested for electrical shorts using a Protek multimeter (Model 6300 5 in 1, Digital Multimeter, obtained from Protek Test and Measurement of Englewood, N.J.).

All tests were performed in air that had been passed over DRIERITE desiccant from W.A. Hammond Drierite Co. Ltd., Xenia, Ohio to remove moisture, and passed over activated carbon to eliminate organic contaminates. Vapor tests were conducted with the specimen disposed within in test chamber into which air having varying levels of relative humidity was introduced.

Specimens were tested for response to various levels of relative humidity at ambient temperature. A simple flow-through delivery system was used to deliver known levels of relative humidity to the capacitive sensor for measurement. PTFE tubing was used throughout the delivery system. The exposure concentrations were generated by 10 L/min flow of air through temperature-controlled evaporation flask containing distilled water. The temperature of the water in the double wall flask was controlled by a Heating/Cooling Circulator from VWR and the air stream of dry air was regulated by a Matheson gas flow meter. The relative humidity in the gaseous stream was monitored with an iTHX-M Humidity Meter available from Omega Engineering Inc., Stamford, Con. The humidified air was introduced into a test chamber (held at controlled temperature) containing the humidity sensor (prepared above). The electrodes of the humidity sensor were connected to an operating circuit that comprised an LCR meter (available as Instek Model 821 LCR meter from Instek America, Corp. Chino, Calif.) using spring loaded probes. The changes in capacitance (in picofarads (pF)) of the capacitive sensor were monitored at a frequency of 1 kHz and 1 V at specific time intervals during the entire course of the water vapor test. The choice of such low operating potential and high perturbation frequency ensured lack of interference from any possible Faradaic processes associated with electrolyzing water present in the measured gas stream.

Specimens (i.e., humidity sensor elements minus the conductive members) were prepared according to the above procedure as shown in TABLE 1 (below).

TABLE 1

| SPECIMEN | DETECTION LAYER THICKNESS, nanometers | BASE CAPACITANCE AT 0% RELATIVE HUMIDITY, pF |
|---|---|---|
| 1 | 708 | 1.6 |
| 2 | 5084 | 1.8 |
| 3 | 2456 | 0.8 |
| 4 | 3361 | 1.8 |
| 5 | 2038 | 1.6 |

Example 1

A 10 percent solids by weight solution of 3M PERFLUOROSULFONIC ACID IONOMER (825 grams per sulfonate equivalent) was prepared by diluting it with methanol. Spin coating was done at 2000 rpm. Before testing, the specimen (Specimen 1) was placed in an oven for 15 min at 150° C. The specimen was evaluated by attaching spring clip probes of an Instek Model 821 LCR meter to the nonporous conductive electrode and the permeable conductive electrode. Humidity exposure showed very good sensor sensitivity over a wide range of relative humidity that was comparable to an Omega iTHX-M Humidity Meter. Measured humidity using the Omega iTHX-M Humidity Meter and measured capacitance values for the humidity sensor under the same conditions are reported in the Table 2 (below).

TABLE 2

| OMEGA ITHX-M HUMIDITY METER, % Relative Humidity | Capacitance of Specimen 1, picofarads |
|---|---|
| 1.7 | 1.59 |
| 8.2 | 1.76 |
| 10.9 | 1.79 |
| 12.5 | 1.83 |
| 18 | 2.11 |
| 27.8 | 4.23 |
| 42.3 | 17 |
| 60.6 | 75 |
| 81.5 | 321 |
| 61.1 | 100 |
| 18.1 | 2.13 |
| 15.4 | 2.02 |
| 10.6 | 1.77 |
| 6.6 | 1.67 |
| 1.4 | 1.58 |
| 1.1 | 1.57 |

Example 2

A 20.2 percent solids by weight solution of 3M PERFLUOROSULFONIC ACID IONOMER (825 grams per sulfonate equivalent) in 60/40 (wt./wt.) n-propanol/water was used in preparation of this specimen (Specimen 2). Spin coating was done at 1000 rpm. Before testing, the specimen was placed in an oven for 15 min at 150° C. The specimen was evaluated by attaching spring clip probes of an Instek Model 821 LCR meter to the nonporous conductive electrode and the permeable conductive electrode. Humidity exposure showed very good sensor sensitivity over a wide range of relative humidity that was comparable to an Omega iTHX-M Humidity Meter. Measured humidity using the Omega iTHX-M Humidity Meter and measured capacitance values for the humidity sensor under the same conditions are reported in the Table 3.

Example 3

A 20.2 percent solids by weight solution of 3M PERFLUOROSULFONIC ACID IONOMER (825 grams per sulfonate equivalent) in 60/40 (wt./wt.) n-propanol/water was used in preparation of this specimen (Specimen 3). Spin coating was done at 2000 rpm resulting in a thinner detection layer than in Specimen 2. Before testing, the specimen was placed in an oven for 15 min at 150° C. The specimen was evaluated by attaching spring clip probes of an Instek Model 821 LCR meter to the nonporous conductive electrode and the permeable conductive electrode. Humidity exposure showed very good sensor sensitivity over a wide range of relative humidity that was comparable to an Omega iTHX-M Humidity Meter. Measured humidity using the Omega iTHX-M Humidity Meter and measure capacitance values for the humidity sensor under the same conditions are reported in the Table 3 (below).

TABLE 3

| OMEGA ITHX-M HUMIDITY METER, % Relative Humidity | CAPACITANCE OF SPECIMEN 3, picofarads | CAPACITANCE OF SPECIMEN 2, picofarads |
|---|---|---|
| 0.6 | 0.78 | 1.42 |
| 10.1 | 2 | 7.2 |
| 16.4 | 8.3 | 42 |
| 33.2 | 96 | 457 |
| 46.9 | 302 | 1377 |
| 57.3 | 573 | 2698 |
| 75.6 | 1798 | 7830 |
| 58.2 | 776 | 3581 |
| 47.6 | 420 | 2024 |
| 33.4 | 128 | 657 |
| 18.5 | 14.3 | 79 |
| 10.4 | 2.4 | 8.6 |
| 1.1 | 0.81 | 1.46 |

Example 4

A 20.2 percent solids by weight solution of 3M PERFLUOROSULFONIC ACID IONOMER (825 grams per sulfonate equivalent) in 60/40 (wt./wt.) n-propanol/water was used in preparation of this specimen (Specimen 4). Spin coating was done at 4000 rpm. Before testing, the specimen was placed in an oven for 15 min at 150° C. The specimen was evaluated by attaching spring clip probes of an Instek Model 821 LCR meter to the nonporous conductive electrode and the permeable conductive electrode. Humidity exposure showed very good sensor sensitivity over a wide range of low relative humidity that was comparable to an Omega iTHX-M Humidity Meter. Measured humidity using the Omega iTHX-M Humidity Meter and measured capacitance values for the humidity sensor under the same conditions are reported in the Table 4.

Example 5

A 20.2 percent solids by weight solution of 3M PERFLUOROSULFONIC ACID IONOMER (825 grams per sulfonate equivalent) in 60/40 (wt./wt.) n-propanol/water was used in preparation of this specimen (Specimen 5). Spin coating was done at 8000 rpm resulting in a thinner detection layer than in Specimen 4. Before testing, the specimen was placed in an oven for 15 min at 150° C. The specimen was evaluated by attaching spring clip probes of an Instek Model 821 LCR meter to the nonporous conductive electrode and the permeable conductive electrode. Humidity exposure showed very good sensor sensitivity over a wide range of low relative humidity that was comparable to an Omega iTHX-M Humidity Meter. Measured humidity using the Omega iTHX-M Humidity Meter and measured capacitance values for the humidity sensor under the same conditions are reported in the Table 4 (below).

TABLE 4

| OMEGA ITHX-M HUMIDITY METER, % Relative Humidity | CAPACITANCE OF SPECIMEN 5, picofarads | CAPACITANCE OF SPECIMEN 4, picofarads |
|---|---|---|
| 0.6 | 1.562 | 1.549 |
| 3.9 | 1.635 | 1.694 |
| 6.6 | 1.752 | 2.045 |
| 9 | 1.963 | 2.774 |
| 11.3 | 2.348 | 4.081 |
| 14.7 | 3.53 | 7.724 |
| 15.7 | 3.973 | 8.997 |
| 14.1 | 3.148 | 6.539 |
| 12 | 2.449 | 4.421 |
| 9.2 | 1.973 | 2.871 |
| 7.7 | 1.819 | 2.355 |
| 1.1 | 1.578 | 1.588 |

Example 6

Example 6 was carried out as in Example 1, except the gold permeable conductive electrode was 7 nm thick and the connecting electrodes were made of 50 nm gold. A 20 percent solids by weight solution of 3M PERFLUOROSULFONIC ACID IONOMER (825 grams per sulfonate equivalent) in 60/40 (weight/weight) n-propanol/water was used in preparation of this specimen (Specimen 6). Spin coating was done at 2500 rpm resulting in a 1,444 nm thick detection layer. Before testing, the specimen was placed in an oven for 15 min at 150° C. The specimen was evaluated by attaching spring clip probes of an Instek Model 821 LCR meter to the nonporous conductive electrode and the permeable conductive electrode. Measured humidity using the Omega iTHX-M Humidity Meter and measured capacitance values for the humidity sensor under the same conditions are reported in the Table 5.

Comparative Example A

Comparative Example A was prepared generally in the same way as Example 6, except that NAFION DE2820 was used in place of the 3M PERFLUOROSULFONIC ACID IONOMER, and spin coating conditions were modified to achieve similar detection layer thickness. A 20 percent solids by weight solution of NAFION DE2820 copolymer was prepared by diluting it with 60/40 (wt./wt.) n-propanol/water. Spin coating was done at 8000 rpm resulting in a 1,433 nm thick detection layer. Before testing, the specimen (Comparative Specimen A) was placed in an oven for 15 min at 150° C. Comparative Specimen A was evaluated by attaching spring clip probes of an Instek Model 821 LCR meter to the nonporous conductive electrode and the permeable conductive electrode. Humidity exposure showed very good sensitivity, but lesser response than comparable 3M PERFLUOROSULFONIC ACID IONOMER-based specimen (Specimen 6).

Measured humidity using the Omega iTHX-M Humidity Meter, and measured capacitance values for Specimen 6 and Comparative Specimen A under the same conditions are reported in the Table 5 (below).

TABLE 5

| OMEGA ITHX-M HUMIDITY METER, % Relative Humidity | CHANGE IN CAPACITANCE OF SPECIMEN 6, nanofarads | CHANGE IN CAPACITANCE OF COMPARATIVE SPECIMEN A, nanofarads |
|---|---|---|
| 0.1 | 657 | 475 |
| 0.5 | 723 | 512 |
| 2.1 | 824 | 545 |
| 6.3 | 1040 | 659 |
| 12.0 | 1266 | 787 |
| 25.0 | 1720 | 1238 |

Select Embodiments of the Present Disclosure

In a first embodiment, the present disclosure provides a humidity sensor element comprising:

a dielectric substrate;

a nonporous conductive electrode having a first conductive member electrically coupled thereto, wherein the nonporous conductive electrode is disposed on the dielectric substrate;

a permeable conductive electrode having a second conductive member electrically coupled thereto, wherein the permeable conductive electrode has a thickness in a range of from 4 to 10 nanometers, wherein the permeable conductive electrode is parallel to the nonporous conductive electrode, and wherein the permeable conductive electrode is permeable by water vapor;

a detection layer sandwiched between the nonporous conductive electrode and the permeable conductive electrode, wherein the detection layer comprises a copolymer having monomeric units comprising

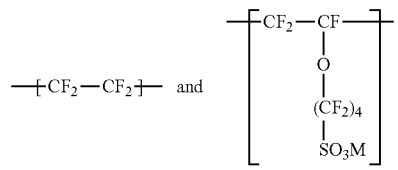

wherein M represents H, or an alkali metal.

In a second embodiment, the present disclosure provides a humidity sensor element according to the first embodiment, wherein the dielectric substrate is nonporous.

In a third embodiment, the present disclosure provides a humidity sensor element according to the first or second embodiment, wherein the dielectric substrate comprises a glass plate.

In a fourth embodiment, the present disclosure provides a humidity sensor element according to any one of the first to third embodiments, wherein the permeable conductive electrode comprises gold.

In a fifth embodiment, the present disclosure provides a humidity sensor element according to any one of the first to fourth embodiments, wherein the nonporous conductive electrode comprises gold.

In a sixth embodiment, the present disclosure provides a humidity sensor element according to any one of the first to fifth embodiments, wherein the copolymer is a random copolymer having a segment represented by the stoichiometric formula

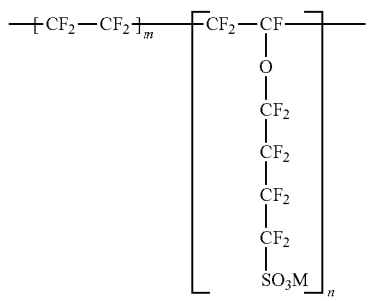

wherein m and n are positive integers, and M is H or an alkali metal.

In a seventh embodiment, the present disclosure provides a humidity sensor element according to any one of the first to sixth embodiments, wherein the copolymer has a sulfonate equivalent weight in a range of from 500 to 1000 grams per sulfonate equivalent.

In an eighth embodiment, the present disclosure provides a humidity sensor comprising:
a sensor chamber having an inlet opening;
a humidity sensor element according to any one of the first to seventh embodiments and having a capacitance, wherein the humidity sensor element is disposed within the sensor chamber in fluid communication with the inlet opening; and
an operating circuit in electrical communication with the first and second conductive leads of the humidity sensor element, whereby if the humidity sensor element is connected to a source of electrical power, the operating circuit measures the capacitance of the sensor element.

In a ninth embodiment, the present disclosure provides a humidity sensor according to the eighth embodiment, wherein the sensor chamber further comprises an outlet opening in fluid communication with the inlet opening.

In a tenth embodiment, the present disclosure provides a humidity sensor element according to the eighth or ninth embodiment, further comprising a display device communicatively coupled with the operating circuit.

Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A humidity sensor element comprising:
a dielectric substrate;
a nonporous conductive electrode having a first conductive member electrically coupled thereto, wherein the nonporous conductive electrode is disposed on the dielectric substrate;
a permeable conductive electrode having a second conductive member electrically coupled thereto, wherein the permeable conductive electrode has a thickness in a range of from 4 to 10 nanometers, wherein the permeable conductive electrode is parallel to the nonporous conductive electrode, and wherein the permeable conductive electrode is permeable by water vapor;
a detection layer sandwiched between the nonporous conductive electrode and the permeable conductive electrode, wherein the detection layer comprises a copolymer having monomeric units comprising

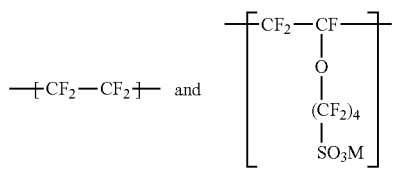

wherein M represents H, or an alkali metal,
wherein the humidity sensor element has a capacitance detectable between the nonporous conductive electrode and the permeable conductive electrode.

2. The humidity sensor element of claim 1, wherein the dielectric substrate is nonporous.

3. The humidity sensor element of claim 1, wherein the dielectric substrate comprises a glass plate.

4. The humidity sensor element of claim 1 wherein the permeable conductive electrode comprises gold.

5. The humidity sensor element of claim 1 wherein the nonporous conductive electrode comprises gold.

6. The humidity sensor element of claim 1 wherein the copolymer is a random copolymer having a segment represented by the stoichiometric formula

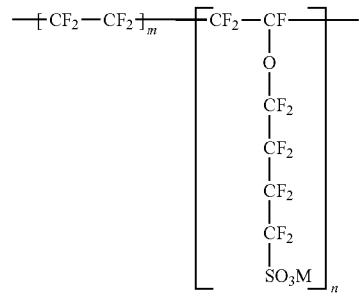

wherein m and n are positive integers, and M is H or an alkali metal.

7. The humidity sensor element of claim 1 wherein the copolymer has a sulfonate equivalent weight in a range of from 500 to 1000 grams per sulfonate equivalent.

8. A humidity sensor comprising:
a sensor chamber having an inlet opening;
a humidity sensor element according to claim 1, wherein the humidity sensor element is disposed within the sensor chamber in fluid communication with the inlet opening; and
an operating circuit in electrical communication with the first and second conductive members of the humidity sensor element, whereby if the humidity sensor element is connected to a source of electrical power, the operating circuit measures the capacitance of the sensor element.

9. The sensor of claim 8, wherein the sensor chamber further comprises an outlet opening in fluid communication with the inlet opening.

10. The sensor of claim 8 further comprising a display device communicatively coupled with the operating circuit.

11. The humidity sensor element of claim 1, wherein the permeable conductive electrode has the thickness in a range of from 5 nm to 9 nm.

12. The humidity sensor element of claim 11, wherein the permeable conductive electrode has the thickness in a range of from 5 nm to 8 nm.

13. The humidity sensor element of claim 11, wherein the permeable conductive electrode has the thickness in a range of from 6 nm to 7 nm.

* * * * *